United States Patent
Itsumi et al.

(10) Patent No.: US 8,156,808 B2
(45) Date of Patent: Apr. 17, 2012

(54) STIFFNESS DETECTOR, STIFFNESS DETECTION METHOD, AND PAPER SHEET PROCESSOR INCLUDING STIFFNESS DETECTOR

(75) Inventors: Kazuhiro Itsumi, Tokyo (JP); Takahiro Yamamoto, Fuchu (JP); Takahisa Nakano, Kawasaki (JP); Seiji Ikari, Yokohama (JP); Junji Miura, Naka-gun (JP); Tsutomu Saito, Yokohama (JP); Takanobu Nishimura, Chigasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 119 days.

(21) Appl. No.: 12/717,383

(22) Filed: Mar. 4, 2010

(65) Prior Publication Data
US 2010/0314300 A1 Dec. 16, 2010

(30) Foreign Application Priority Data
Jun. 11, 2009 (JP) ................. 2009-140375

(51) Int. Cl.
*G01N 3/40* (2006.01)
(52) U.S. Cl. .................. 73/573; 73/78; 73/577; 73/760
(58) Field of Classification Search .......... 73/1.37–1.38, 73/865.8, 573, 78, 577, 643, 760; 702/96, 702/116
See application file for complete search history.

(56) References Cited

U.S. PATENT DOCUMENTS

| | | | | |
|---|---|---|---|---|
| 4,596,152 A | * | 6/1986 | Lehtikoski et al. | 73/835 |
| 4,869,101 A | * | 9/1989 | Dvorsky | 73/159 |
| 5,182,722 A | * | 1/1993 | Hain | 700/223 |
| 5,922,959 A | * | 7/1999 | Kayani | 73/597 |
| 6,092,421 A | * | 7/2000 | Bar-Cohen et al. | 73/624 |
| 6,407,964 B1 | * | 6/2002 | Hornung et al. | 367/138 |
| 6,543,288 B1 | * | 4/2003 | Blouin et al. | 73/643 |
| 6,574,569 B1 | * | 6/2003 | Omata et al. | 702/33 |
| 6,595,060 B2 | * | 7/2003 | Wunderer et al. | 73/597 |
| 7,194,916 B2 | * | 3/2007 | Ouellet et al. | 73/852 |
| 7,583,413 B2 | * | 9/2009 | Nojiri et al. | 358/3.24 |
| 2008/0302188 A1 | | 12/2008 | Yabushita et al. | |
| 2011/0001285 A1 | * | 1/2011 | Yamamoto et al. | 271/264 |

FOREIGN PATENT DOCUMENTS

| | | |
|---|---|---|
| FR | 2 661 749 | 11/1991 |
| JP | 08-273020 | 10/1996 |
| JP | 2001-330423 | 11/2001 |
| JP | 2006-250869 | 9/2006 |
| JP | 2007-010638 | 1/2007 |
| JP | 3993366 B2 | 8/2007 |
| JP | 2008-164394 | 7/2008 |
| SU | 589577 | 1/1978 |

OTHER PUBLICATIONS

European Search Report dated Sep. 9, 2010.
Takahiro Yamamoto, U.S. Appl. No. 12/717,357.

\* cited by examiner

*Primary Examiner* — J M Saint Surin
(74) *Attorney, Agent, or Firm* — Pillsbury Winthrop Shaw Pittman, LLP

(57) ABSTRACT

A stiffness detector transmits acoustic waves to a paper sheet at a predetermined angle to excite Lamb waves. The stiffness detector receives leaky waves of the Lamb waves propagated through the paper sheet at different angles with respect to the paper sheet by a plurality of reception sensors. The stiffness detector is configured to specify a maximum leak angle at which a leak amount of the acoustic waves from the paper sheet becomes maximum based on outputs from the plurality of reception sensors in the reception module and to judge a degree of fatigue of the paper sheet based on the specified maximum leak angle.

7 Claims, 11 Drawing Sheets

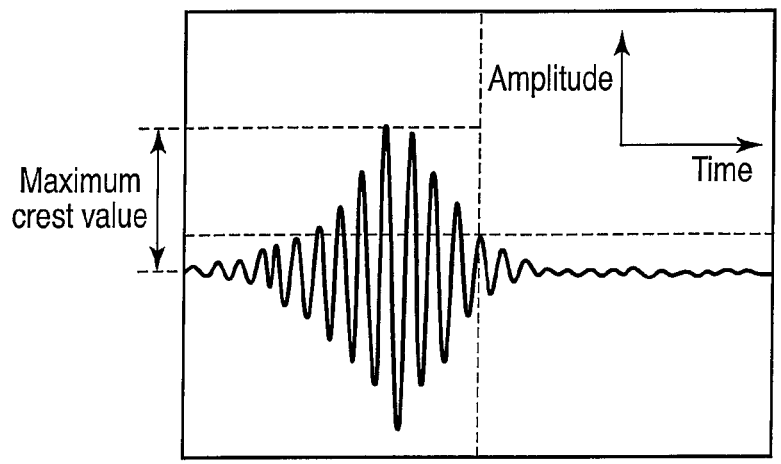
F I G. 9
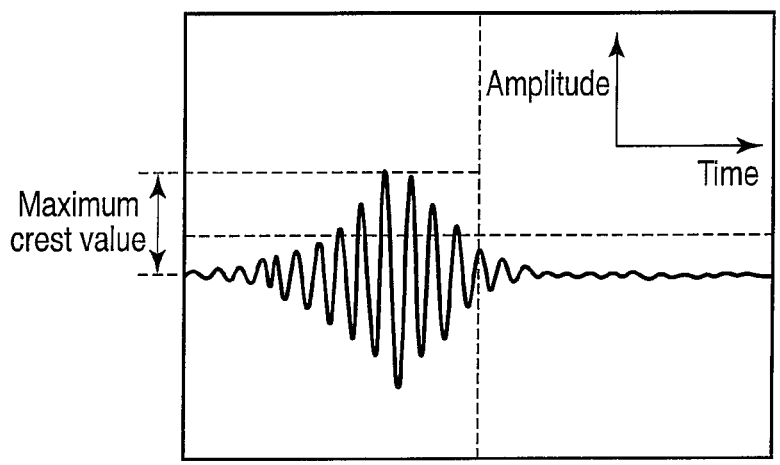
F I G. 10
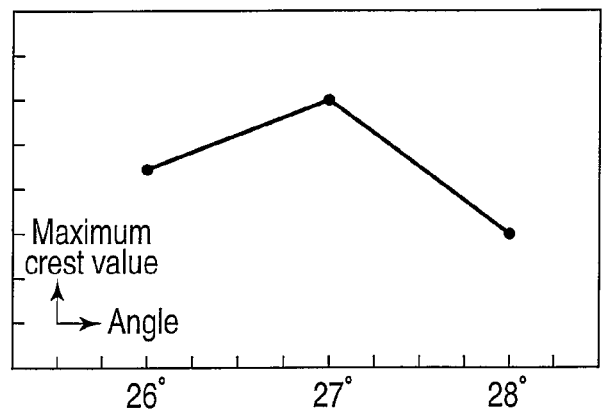
F I G. 11

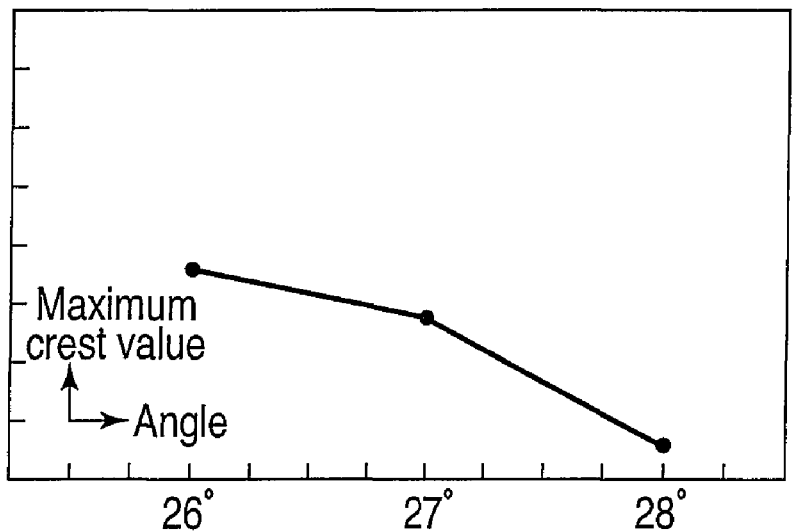
F I G. 12
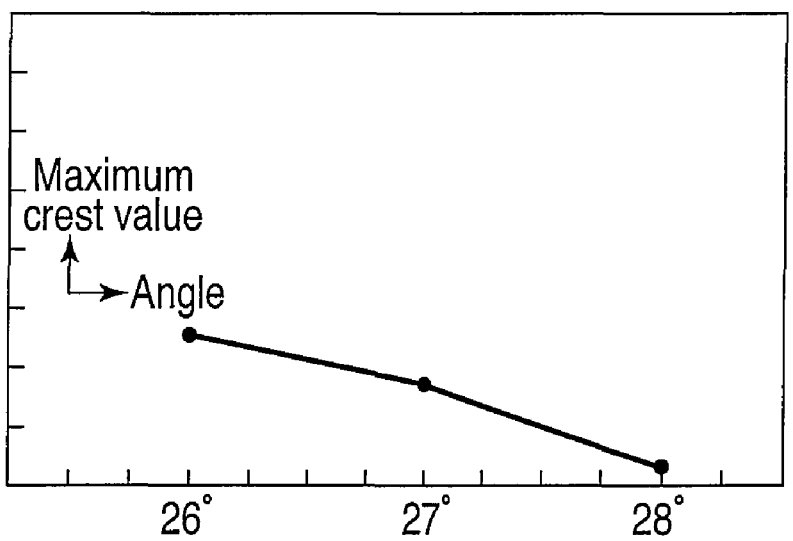
F I G. 13

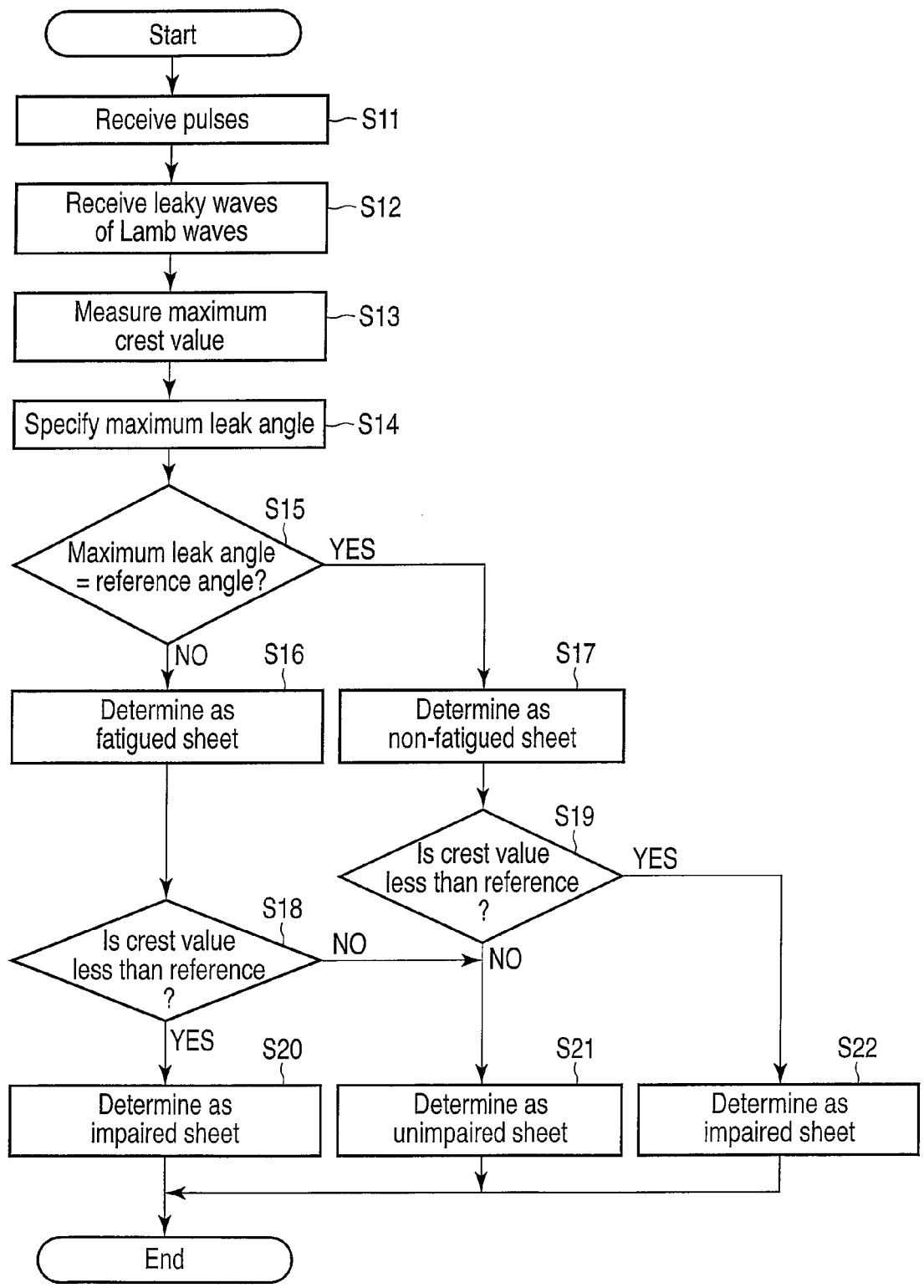
F I G. 14

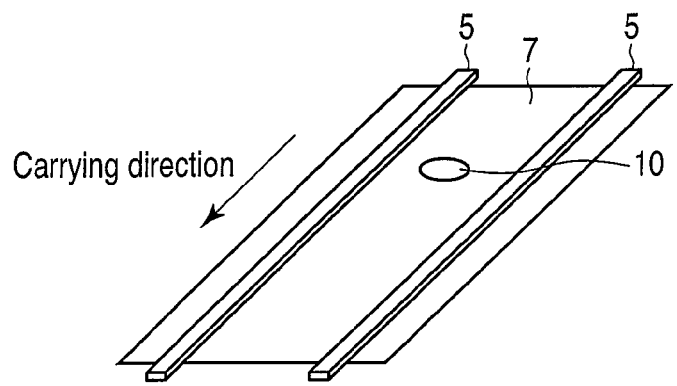
F I G. 15
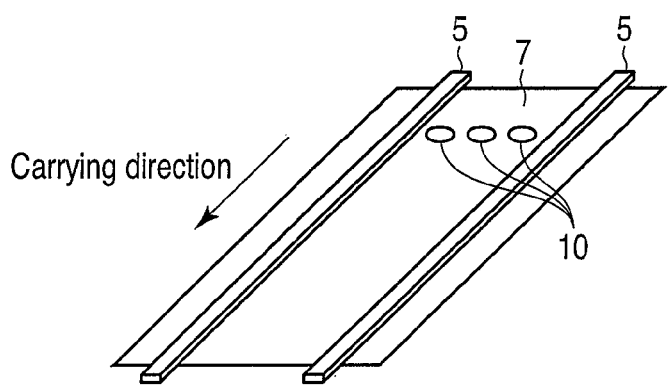
F I G. 16
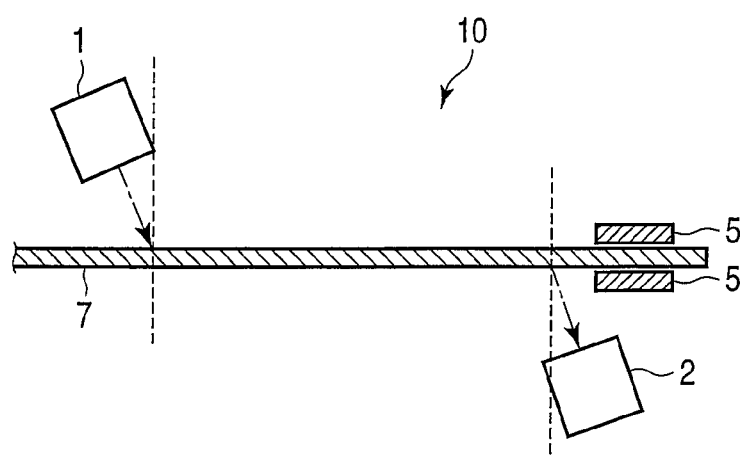
F I G. 17

STIFFNESS DETECTOR, STIFFNESS DETECTION METHOD, AND PAPER SHEET PROCESSOR INCLUDING STIFFNESS DETECTOR

CROSS-REFERENCE TO RELATED APPLICATIONS

This application is based upon and claims the benefit of priority from prior Japanese Patent Application No. 2009-140375, filed Jun. 11, 2009, the entire contents of which are incorporated herein by reference.

BACKGROUND OF THE INVENTION

1. Field of the Invention

The present invention relates to a stiffness detector that detects stiffness of a paper sheet such as a paper currency, a stiffness detection method, and a paper sheet processor including the stiffness detector.

2. Description of the Related Art

A paper sheet processor that counts and discriminates various kinds of paper sheets such as a paper currency have been put to practical use. The paper sheet processor takes paper sheets put in an injection module one by one and carries them to an examination device for paper sheets. The examination device executes various kinds of processing with respect to paper sheets to judge states of the paper sheets. The paper sheet processor executes a judgment on a type of each paper sheet, a true-false judgment, a wear judgment of judging whether a paper sheet can be again circulated, and others based on an examination result obtained by the examination device.

The examination device detects mechanical characteristics such as a degree of degradation in stiffness of paper sheets. The paper sheet processor determines paper sheets having degraded stiffness as paper sheets that are not suitable for recirculation.

For example, Jpn. Pat. Appln. KOKAI Publication No. 2006-250869 as a Japanese patent document discloses a technology for applying ultrasonic waves to a paper sheet and detecting a characteristic frequency of the paper sheet from radiation waves from the paper sheet to judge degradation in stiffness of the paper sheet.

Further, Jpn. Pat. Appln. KOKAI Publication No. 1996-273020 as a Japanese patent document discloses a technology for dynamically measuring both or one of a thickness and a weighing capacity of a moving material. Furthermore, Jpn. Pat. Appln. KOKAI Publication No. 2001-330423 as a Japanese patent document discloses a technology for detecting a state that two paper sheets have been taken at the same time based on a phase shift and an amplitude of ultrasonic waves. Moreover, Japanese patent No. 3993366 as a Japanese patent document discloses a technology for installing a wave transmitter and a wave receiver to sandwich a carrier path and detecting a state that two paper sheets have been taken at the same time based on acoustic waves that enter the wave receiver.

Additionally, Jpn. Pat. Appln. KOKAI Publication No. 2007-10638 and Jpn. Pat. Appln. KOKAI Publication No. 2008-164394 as a Japanese patent document discloses a technology for causing ultrasonic waves to enter a sample such as a metal plate, receiving leaky waves of waves that propagate through the sample and detecting a defect in the sample based on an amplitude of a received waveform.

The paper sheet processor carries paper sheets at a high speed and performs examination during carriage. However, the technology disclosed in Jpn. Pat. Appln. KOKAI Publication No. 2006-250869 has a problem that measurement and an arithmetic operation require time since a characteristic frequency of a general paper sheet is low.

Further, according to the technologies disclosed in Jpn. Pat. Appln. KOKAI Publication No. 1996-273020, Jpn. Pat. Appln. KOKAI Publication No. 2001-330423 and Japanese patent No. 3993366, a paper sheet is irradiated with ultrasonic waves and, e.g., a thickness, a weight, multiplicity, or presence/absence of foreign particles of the paper sheet is detected based on reflected or transmitted waves. These technologies do not provide a configuration for measuring an elastic modulus (stiffness) of the paper sheet. Therefore, they have a problem that a degree of degradation in stiffness of the paper sheet cannot be judged.

Furthermore, the technologies disclosed in Jpn. Pat. Appln. KOKAI Publication No. 2007-10638 and Jpn. Pat. Appln. KOKAI Publication No. 2008-164394 have a problem that a factor of a defect cannot be specified when detecting the defect in a sample. That is, they have a problem that a factor of a detected defect which may be a reduction in an elastic modulus, breakage, crack, or crease cannot be determined.

Additional objects and advantages of the embodiments will be set forth in the description which follows, and in part will be obvious from the description, or may be learned by practice of the invention. The objects and advantages of the invention may be realized and obtained by means of the instrumentalities and combinations particularly pointed out hereinafter.

BRIEF SUMMARY OF THE INVENTION

According to one embodiment of the invention, a stiffness detector, a stiffness detection method, a paper sheet processor can be provided, all of which highly accurately detect the stiffness of paper sheets.

A stiffness detector, which is an embodiment of this invention, comprising: a transmission module configured to transmit acoustic waves to a paper sheet at a predetermined angle and thereby excite Lamb waves; a reception module including a plurality of reception sensors which receive leaky waves of the Lamb waves propagated through the paper sheet at different angles with respect to the paper sheet; and a first judgment module configured to specify a maximum leak angle at which a leak amount of the acoustic waves from the paper sheet becomes maximum based on outputs from the plurality of reception sensors in the reception module and to judge a degree of fatigue of the paper sheet based on the specified maximum leak angle.

A stiffness detection method, which is an embodiment of this invention, comprising: transmitting acoustic waves to a paper sheet at a predetermined angle to excite Lamb waves; receiving leaky waves of the Lamb waves propagated through the paper sheet at a plurality of different angles with respect to the paper sheet; and specifying a maximum leak angle at which a leak amount of the acoustic waves from the paper sheet becomes maximum based on signals received at the plurality of angles and judging a degree of fatigue of the paper sheet based on the specified maximum leak angle.

A paper sheet processor, which is an embodiment of this invention, comprising: a carriage module configured to carry a paper sheet; a transmission module configured to transmit acoustic waves to a paper sheet carried by the carriage module at a predetermined angle and thereby excite Lamb waves; a reception module including a plurality of reception sensors which receive leaky waves of the Lamb waves propagated through the paper sheet at different angles with respect to the paper sheet; a judgment module configured to specify a maximum leak angle at which a leak amount of acoustic waves from the paper sheet becomes maximum based on outputs from the plurality of reception sensors in the reception module and judge a degree of fatigue of the paper sheet based on the specified maximum leak angle; and a classification processing module configured to classify the paper sheet based on a judgment result obtained by the judgment module.

Thus, this invention can provide a stiffness detector, a stiffness detection method, a paper sheet processor can be provided, all of which highly accurately detect the stiffness of paper sheets.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

FIG. 9 is an explanatory view for explaining an example of a waveform received by the reception module depicted in FIG. 4;

FIG. 10 is an explanatory view for explaining an example of a waveform received by the reception module depicted in FIG. 5;

FIG. 11 is an explanatory view for explaining a relationship between a crest value of a waveform received by each reception module and an angle of the reception module in the stiffness detector;

FIG. 12 is an explanatory view for explaining a relationship between a crest value of a waveform received by each reception module and an angle of the reception module in the stiffness detector;

FIG. 13 is an explanatory view for explaining a relationship between a crest value of a waveform received by each reception module and an angle of the reception module in the stiffness detector;

FIG. 14 is a flowchart for explaining an operation of the stiffness detector;

FIG. 15 is an explanatory view for explaining an example of an arrangement position of the stiffness detector;

FIG. 16 is an explanatory view for explaining an example of an arrangement position of the stiffness detector;

FIG. 17 is an explanatory view for explaining another example of arrangement of the transmission module and the reception module in the stiffness detector;

DETAILED DESCRIPTION OF THE INVENTION

A stiffness detector, a stiffness detection method, and a paper sheet processor including the stiffness detector according to an embodiment of the present invention will now be described hereinafter in detail with reference to the drawings.

Figure 1:
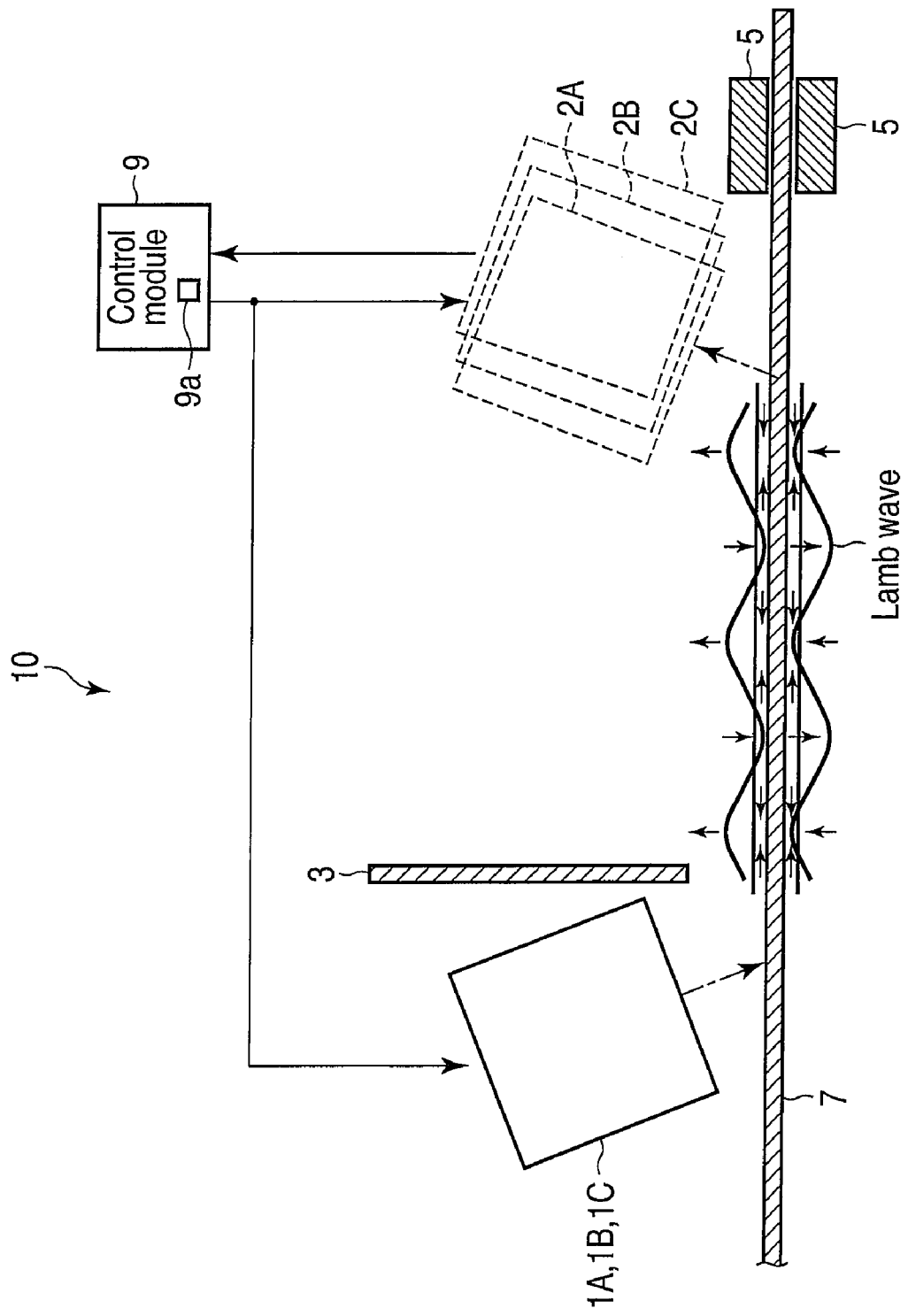
FIG. 1 is an explanatory view for explaining a structural example of a stiffness detector according to an embodiment.

FIG. 1 is an explanatory view for explaining a structural example of a stiffness detector according to an embodiment.

The stiffness detector 10 checks mechanical properties of a paper sheet 7. For example, the stiffness detector 10 detects stiffness such as an elastic modulus, tensile strength or bending strength of the paper sheet 7.

As shown in FIG. 1, the stiffness detector 10 includes a transmission module 1, a reception module 2, a shielding plate 3 and a control module 9. The transmission module 1, the reception module 2 and the shielding plate 3 are disposed on one surface side of the paper sheet 7 to be carried.

The transmission module 1 includes a plurality of transmission modules 1A, 1B and 1C. The transmission module 1 is a transmitter of ultrasonic waves that excite Lamb waves (plate waves) in the paper sheet 7. The transmission module 1 includes, e.g., a speaker, a piezoelectric transducer or a vibration generator using a micro electro mechanical system (MEMS). The transmission module 1 vibrates an vibration plane in accordance with an applied voltage, thereby generating acoustic waves.

The reception module 2 includes a plurality of reception modules (reception sensors) 2A, 2B and 2C. The reception module 2 is a receiver that detects a waveform of the Lamb waves generated in the paper sheet 7. The reception module 2 has the same configuration as the transmission module 1. The reception module 2 includes, e.g., a microphone, a piezoelectric transducer, a displacement gauge (an interferometer) using interfering light that measures vibration as displacement, and others. The reception unit 2 obtains a voltage in accordance with vibration of a vibration plane excited by waves leaking from the paper sheet 7.

It is to be noted that, as shown in FIG. 1, the transmission module 1 and the reception module 2 are disposed near conveying belts 5. The paper sheet 7 is conveyed in a stable state with less slack near the conveying belts 5. Examination can be carried out in the stable state by arranging the transmission module 1 and the reception module 2 in this manner.

The shielding plate 3 shields against acoustic waves (airborne ultrasonic components) propagated to the reception module 2 from the transmission module 1 through air. As a result, crosstalk can be avoided. The shielding plate 3 is formed by bonding, e.g., a sponge to a thin plate of aluminum.

It is to be noted that the any material can be used to form the shielding plate 3 as long as it shields against waves.

The control module 9 controls the entire stiffness detector 10. The control module 9 includes, a CPU, a buffer memory, a program memory, a nonvolatile memory and others. The CPU executes various kinds of arithmetic processing. The buffer memory temporarily stores arithmetic results. The program memory and the nonvolatile memory store various kinds of programs executed by the CPU, control data and others. The control module 9 can execute various kinds of processing by using the CPU to perform a program stored in the program memory. For example, the control module 9 control operation timings of the transmission module 1 and the reception module 2.

The stiffness detector 10 detects stiffness of the paper sheet 7 to be carried. Therefore, the stiffness detector 10 is installed near the conveying belts 5.

The conveying belts 5 function as a conveyance module. The conveying belts 5 include a pair of upper and lower belts as shown in FIG. 1. The conveying belts 5 are driven by a driving pulley or the like. The conveying belts 5 use the pair of upper and lower belts to sandwich the paper sheet 7 and convey it at a fixed speed.

When detecting the paper sheet 7, the stiffness detector 10 generates ultrasonic waves from the transmission module 1. As a result, the stiffness detector 10 applies ultrasonic waves to the paper sheet 7. In the paper sheet 7, the Lamb waves are excited by the ultrasonic waves. The excited Lamb waves generate leaky waves from a surface of the paper sheet 7 while being propagated through the paper sheet 7. The stiffness detector 10 detects the leaky waves of the Lamb waves by using the reception module 2.

As shown in FIG. 1, the Lamb wave is a wave whose vibrating direction is vertical to a medium and which is propagated in a propagating direction with the same vibration component. The Lamb wave is a wave that is propagated through a medium having substantially the same thickness as a wavelength. The Lamb wave has characteristics that it can be detected at any point in the medium through which this wave is propagated, its acoustic velocity can be calculated from a propagation time, it is affected when a medium is not uniform, or a signal intensity does not fluctuate when narrowed, for example. It is to be noted that FIG. 1 shows a state of propagation of the Lamb waves in an asymmetrical mode.

The paper sheet 7 is constituted of fibers and a binder. However, when the paper sheet 7 is fatigued, the binder becomes deficient, and a contained amount of air relatively increases. As a result, a density of the fatigued paper sheet 7 is lower than that of a non-fatigued paper sheet. When a ratio of air in the paper sheet 7 increases, properties of air become closer to properties of the paper sheet 7, thereby lowering an acoustic resistance value. That is, the Lamb waves propagated through the paper sheet 7 are apt to leak to the outside. Therefore, the Lamb waves are attenuated and an amplitude thereof is reduced before reaching a detection point of the reception module 2.

Furthermore, when emitting ultrasonic waves to the paper sheet 7 from the transmission module 1, the transmission module 1 emits acoustic waves to the paper sheet 7 at an optimum incidence angle θ for the surface of the paper sheet 7. As a result, the amplitude of the Lamb waves generated in the paper sheet 7 becomes maximum. Moreover, a leak amount of the leaky waves of the Lamb waves propagated through the paper sheet 7 varies in accordance with an angle (an output angle) at which the leaky waves exit from the paper sheet 7. The leak amount becomes maximum at the same output angle as the optimum incidence angle (a maximum leak angle).

The optimum incidence angle θ is determined based on air and characteristics of the paper sheet to be examined. Assuming that a velocity of sound propagated through air is Ca and a velocity of sound propagated through the paper sheet 7 is Cs, the optimum incidence angle θ can be determined based on the following Expression 1.

$$\sin\theta = \frac{Ca}{Cs} \qquad \text{(Expression 1)}$$

It is to be noted that the respective acoustic velocities Ca and Cs are determined based on the following Expression 2.

$$\text{velocities } C = \sqrt{\frac{\text{stiffness}}{\text{density}}} \qquad \text{(Expression 2)}$$

As described above, in case of the fatigued paper sheet 7, a velocity of the waves propagated through the paper sheet is reduced. As a result, a value of sine varies, and the optimum incidence angle θ changes. When the properties of the paper sheet 7 have come closer to those of air, the density is reduced, and hence the optimum incidence angle θ is decreased. Therefore, in this embodiment, the maximum leak angle of the non-fatigued paper sheet 7 is determined as a reference angle, and the reception modules 2A, 2B and 2C are disposed at a plurality of different angles. In this case, for example, the reception module 2A is disposed at an angle corresponding to the reference angle+N degrees, the reception module 2B is disposed at the reference angle, and the reception module 2C is disposed at an angle corresponding to the reference angle−M degrees.

It is to be noted that the description will be given on the assumption that the reference angle of the non-fatigued paper sheet 7 is 27 degrees in this embodiment. Moreover, the explanation will be given on the assumption that N=M=1 is achieved.

As described above, the control module 9 in the stiffness detector 10 according to this embodiment judges whether the paper sheet 7 is a fatigued sheet based on a maximum crest value and an installation angle of the reception module 2 that has detected the maximum crest value. Therefore, the control module 9 includes a reference crest value storage module 9a that stores a value of a reference crest value.

Figure 2:
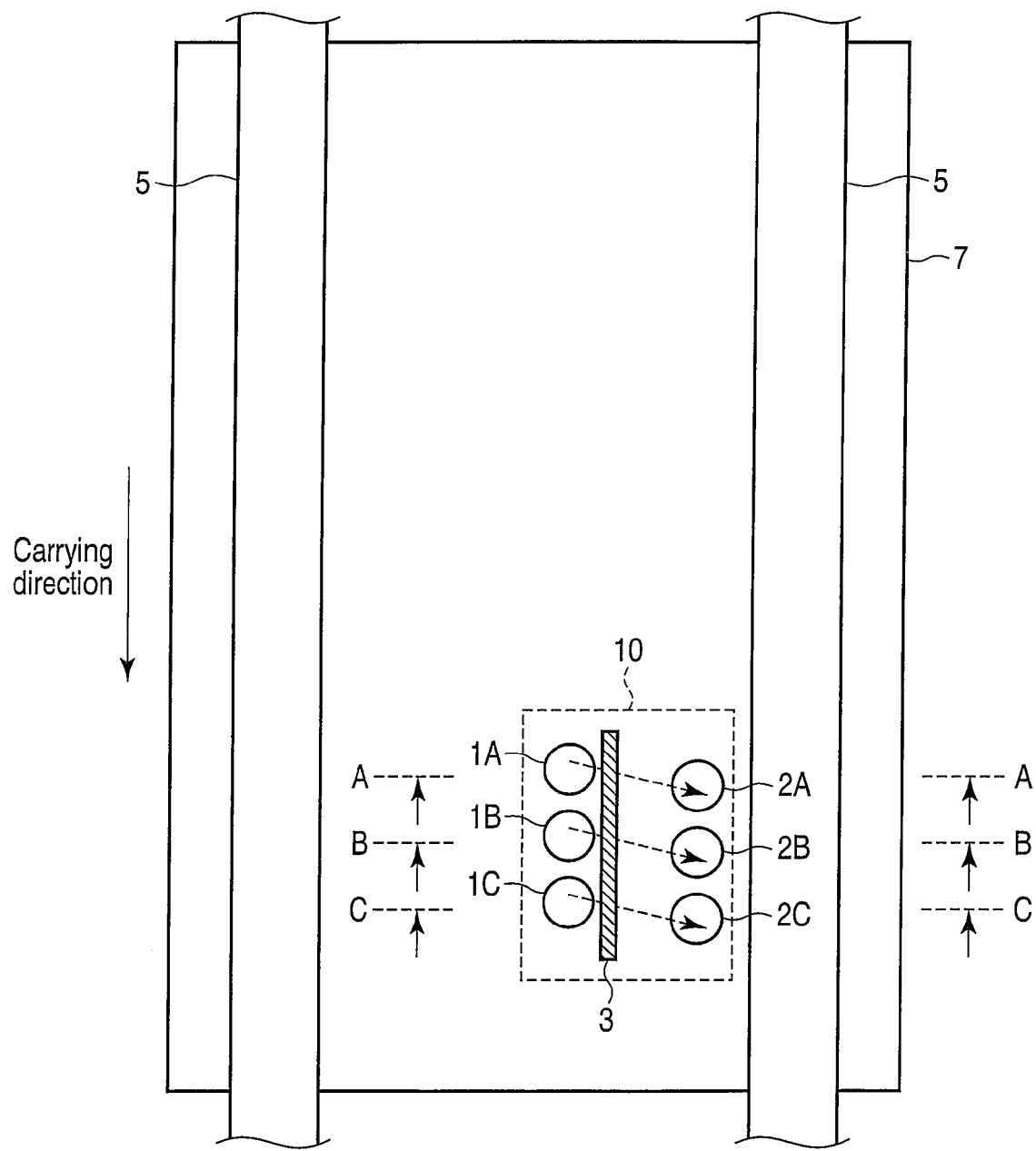
FIG. 2 is an explanatory view for explaining the structural example of the stiffness detector depicted in FIG. 1.

FIG. 2 is a view showing the stiffness detector 10 depicted in FIG. 1 from above.

As shown in FIG. 2, the stiffness detector 10 includes the transmission module 1A, the transmission module 1B and the transmission module 10 aligned and disposed along a carrying direction of the paper sheet 7. Additionally, the stiffness detector 10 includes the reception module 2A, the reception module 2B and the reception module 2C aligned and disposed along the carrying direction of the paper sheet 7.

A pair of the transmission module 1A and the reception module 2A, a pair of the transmission module 1B and the reception module 2B and a pair of the transmission module 10 and the reception module 2C are provided in associated with each other, respectively. That is, the reception module 2A receives the leaky waves of the Lamb waves excited by the ultrasonic waves emitted from the transmission module 1A. Further, the reception module 2B receives the leaky waves of the Lamb waves excited by the ultrasonic waves emitted from the transmission module 1B. Furthermore, the reception module 2C receives the leaky waves of the Lamb waves excited by the ultrasonic waves emitted from the transmission module 1C.

Figure 3:
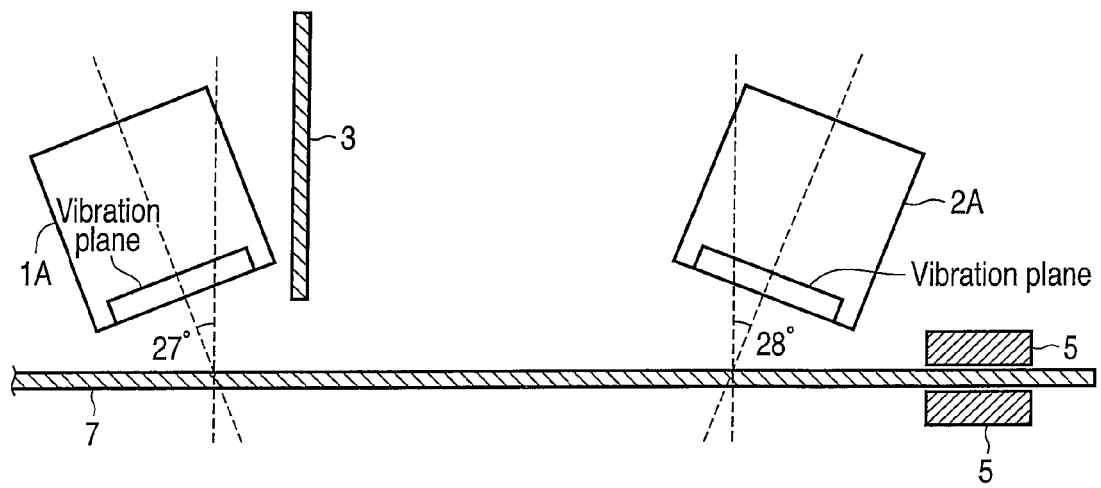
FIG. 3 is an explanatory view for explaining an example of arrangement of each module in the stiffness detector.
Figure 4:
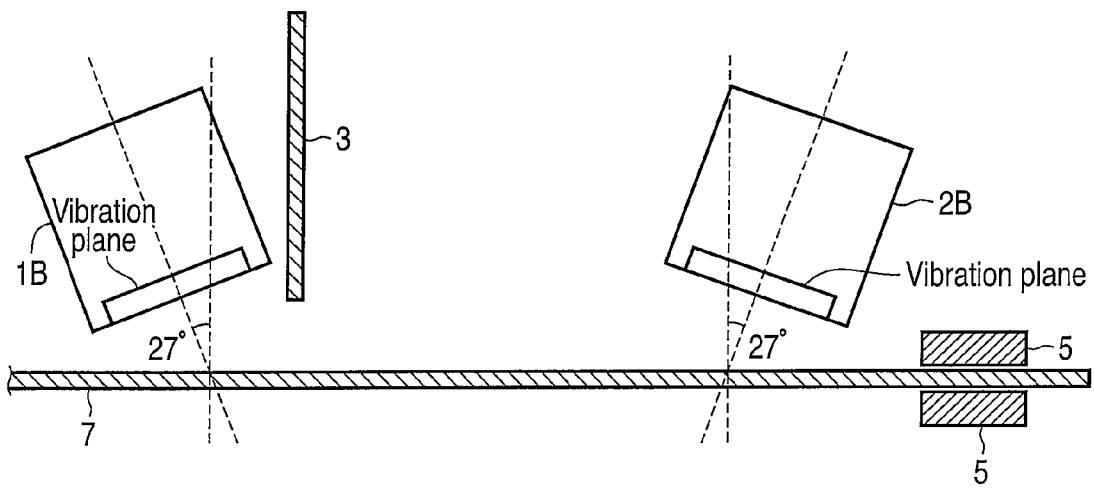
FIG. 4 is an explanatory view for explaining an example of arrangement of each module in the stiffness detector.
Figure 5:
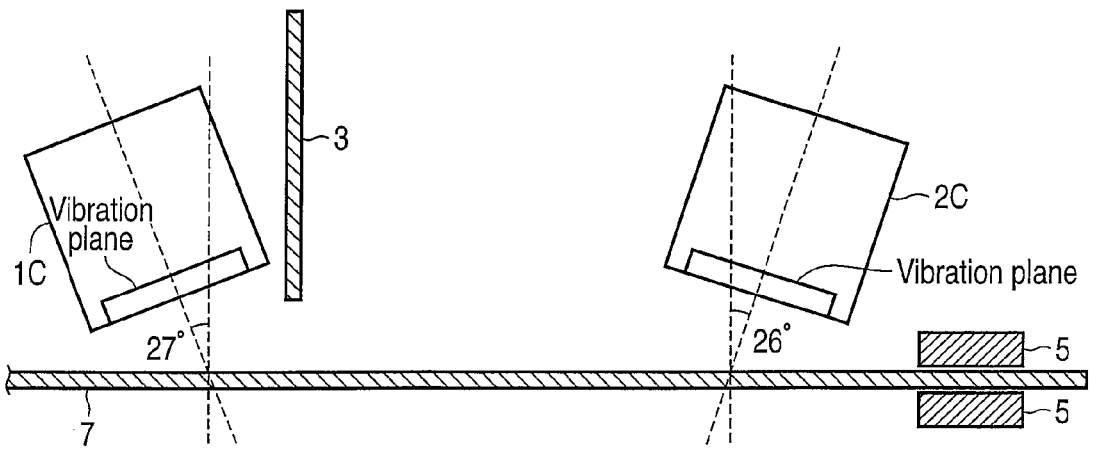
FIG. 5 is an explanatory view for explaining an example of arrangement of each module in the stiffness detector.

FIGS. 3 to 5 are cross-sectional views for explaining arrangement of the transmission module 1 and the reception module 2 in the stiffness detector 10. FIG. 3 is a cross-sectional view of the stiffness detector 10 depicted in FIG. 2 taken along a line AA. Moreover, FIG. 4 is a cross-sectional view of the stiffness detector 10 depicted in FIG. 2 taken along a line BB. Additionally, FIG. 5 is a cross-sectional view of the stiffness detector 10 depicted in FIG. 2 taken along a line CC.

As shown in FIG. 3, the transmission module 1A is disposed in such a manner that a traveling direction of the acoustic waves emitted from the vibration plane of the transmission module 1A and the paper sheet 7 form an angle of 27 degrees. Further, the reception module 2A is disposed in such a manner that a line perpendicular to the vibration plane of the reception module 2A and the paper sheet 7 form an angle of 28 degrees.

Furthermore, as shown in FIG. 4, the transmission module 1B is disposed in such a manner that a traveling direction of the acoustic waves emitted from the vibration plane of the transmission module 1B and the paper sheet 7 form an angle of 27 degrees. Moreover, the reception module 2B is disposed in such a manner that a line perpendicular to the vibration plane of the reception module 2B and the paper sheet 7 form an angle of 27 degrees.

Additionally, as shown in FIG. 5, the transmission module 10 is disposed in such a manner that a traveling direction of the acoustic waves emitted from the vibration plane of the transmission module 1C and the paper sheet 7 form an angle of 27 degrees. Further, the reception module 2C is disposed in such a manner that a line perpendicular to the vibration plane of the reception module 2C and the paper sheet 7 form an angle of 26 degrees.

That is, arranging the reception modules 2A, 2B and 2C as described above enables detecting the leaky waves of the Lamb waves propagated through the paper sheet 7 at the different angles.

Figure 6:
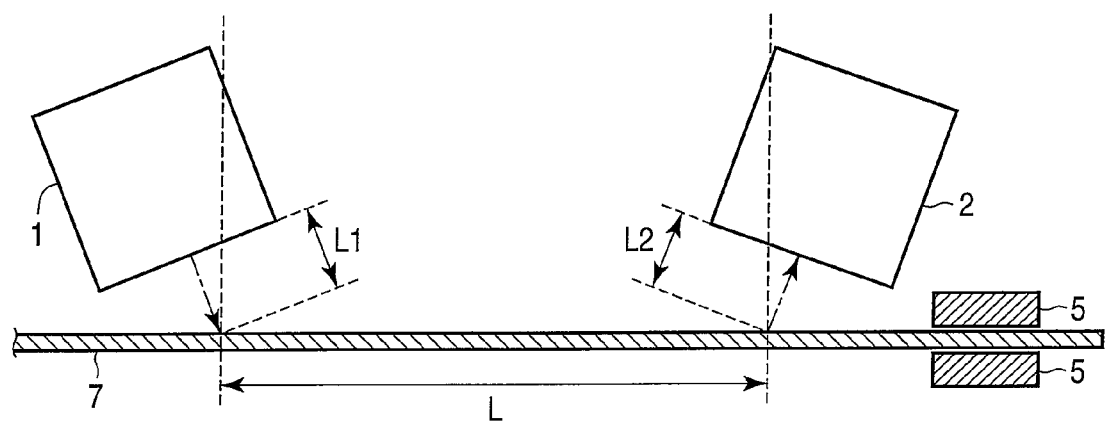
FIG. 6 is an explanatory view for explaining an example of arrangement of a transmission module and a reception module in the stiffness detector.
Figure 7:
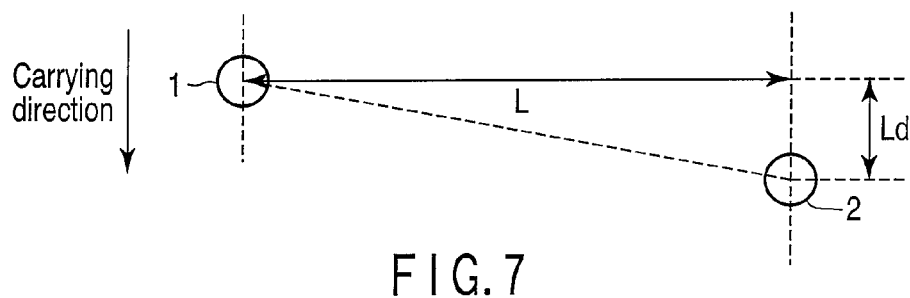
FIG. 7 is an explanatory view for explaining an example of arrangement of the transmission module and the reception module in the stiffness detector.

FIGS. 6 and 7 are cross-sectional views for explaining arrangement of the transmission module and the reception module in the stiffness detector. Here, the description will be given by using a pair of the transmission module 1 and the reception module 2.

As shown in FIG. 6, the transmission module 1 and the reception module 2 are disposed at a predetermined interval therebetween in a direction perpendicular to the carrying direction of the paper sheet 7. Therefore, a timing at which the acoustic waves are emitted from the transmission module 1 in the stiffness detector deviates from a timing at which the waves are detected from the paper sheet 7 by the reception module 2. That is, when the paper sheet 7 is carried, a detection point of the reception module 2 deviates in the carrying direction in accordance with a carrying velocity.

Therefore, as shown in FIG. 7, the transmission module 1 and the reception module 2 are arranged to be staggered by a predetermined distance (a distance Ld) along the carrying direction of the paper sheet 7.

The carrying velocity of the paper sheet 7 is determined as v. Furthermore, a time from emission of the acoustic waves from the transmission module 1 to detection of the waves by the reception module 2 is t. In this case, the distance Ld can be determined based on the following Expression 3.

$$Ld = v \times t$$ (Expression 3)

Moreover, as shown in FIG. 6, a distance between an incidence point at which incidence of the acoustic waves is performed by the transmission module 1 and the detection point at which the reception module 2 detects the waves is L. Additionally, a distance between the transmission module 1 and the paper sheet 7 is L1, and a distance between the reception module 2 and the paper sheet 7 is L2. In this case, a time from emission of the acoustic waves from the transmission module 1 to detection of the waves by the reception module 2 can be determined based on the following Expression 4.

$$t = \frac{L1}{Ca} + \frac{L}{Cs} + \frac{L2}{Ca}$$ (Expression 4)

Figure 8:
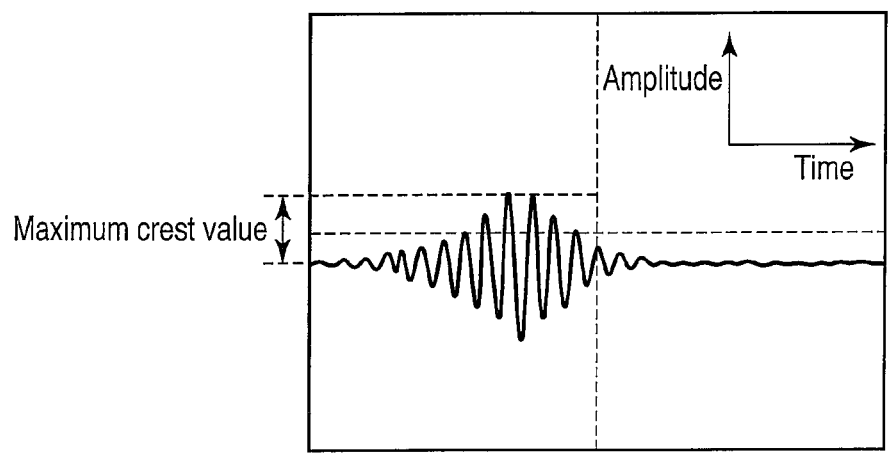
FIG. 8 is an explanatory view for explaining an example of a waveform received by the reception module depicted in FIG. 3.

FIGS. 8 to 10 are views each showing a waveform of the waves received by the reception module 2.

FIG. 8 is an explanatory view for explaining an example of the waveform received by the reception module 2A depicted in FIG. 3. FIG. 9 is an explanatory view for explaining an example of a waveform received by the reception module 2B shown in FIG. 4. FIG. 10 is an explanatory view for explaining an example of the waveform received by the reception module 2C shown in FIG. 5. It is to be noted that results of examination with respect to the non-fatigued paper sheet 7 will be described herein.

That is, the waveform depicted in FIG. 8 is a waveform of the leaky waves of the Lamb waves received by the reception module 2A installed at the angle of 28 degrees with respect to the paper sheet 7. Furthermore, the waveform shown in FIG. 9 is a waveform of the leaky waves of the Lamb waves received by the reception module 2B installed at the angle of 27 degrees with respect to the paper sheet 7. Moreover, the waveform shown in FIG. 10 is a waveform of the leaky waves of the Lamb waves received by the reception module 2C installed at the angle of 26 degrees with respect to the paper sheet 7.

A graph shown in each of FIGS. 8 to 10 shows a waveform of the leaky waves from the paper sheet 7. An abscissa represents a time, and an ordinate represents an amplitude of the waves.

As shown in FIGS. 8 to 10, the waveform received by the reception module 2B has the largest amplitude (a maximum crest value). The waveform received by the reception module 2C has the second largest maximum crest value, and the waveform received by the reception module 2A has the smallest maximum crest value.

For example, when the paper sheet 7 is fatigued, the maximum leak angle becomes small. Therefore, the waveform received by the reception module 2C has the largest maximum crest value. The waveform received by the reception module 2B has the second largest maximum crest value, and the waveform received by the reception module 2A has the smallest maximum crest value.

Each of FIGS. 11 to 13 is an explanatory view for explaining a relationship between the maximum crest value of the waveform received by the reception module 2 and an installation angle of the reception module 2 in the stiffness detector 10.

FIG. 11 is a view showing a relationship between the maximum crest value in a result of examination conducted with respect to the non-fatigued paper sheet 7 and an installation angle of the reception module 2. FIG. 12 is a view showing a relationship between the maximum crest value in a result of examination conducted with respect to the fatigued paper sheet 7 and an installation angle of the reception module 2. FIG. 13 is a view showing a relationship between the maximum crest value in a result of examination conducted with respect to the paper sheet 7 more fatigued than the paper sheet 7 in the example shown in FIG. 12 and an installation angle of the reception module 2.

The control module 9 in the stiffness detector 10 judges a degree of fatigue and wear of the paper sheet 7 based on the relationship between the maximum crest value of the waveform received by the reception module 2 and the installation angle of the reception module 2. That is, control module 9 functions as a judgment module. The control module 9 specifies an angle at which a leak amount becomes maximum, i.e., the installation angle of the reception module 2 that has detected the largest maximum crest value as a maximum leak angle. The control unit 9 compares the specified maximum leak angle with a reference angle previously determined based on characteristics of the paper sheet 7. That is, the control module 9 functions as an angle comparison module.

When the maximum leak angle coincides with the reference angle, the control module 9 determines that the paper sheet 7 is not fatigued. Additionally, when the maximum leak angle does not coincide with the reference angle, the control module 9 determines that the paper sheet 7 is fatigued.

As shown in FIG. 11, the reception module 2B installed with respect to the paper sheet 7 at the angel of 27 degrees (the reference angle) detects the largest maximum crest angle. In this case, the control module 9 specifies the installation angle of 27 degrees of the reception module 2B as the maximum leak angle. When the maximum leak angle coincides with the reference angle, the control module 9 determines that the paper sheet 7 is not fatigued.

Further, as shown in FIGS. 12 and 13, the reception module 2C installed at the angle of 26 degrees (an angle that is not the reference angle) with respect to the paper sheet 7 detects the largest maximum crest value. In this case, the control module 9 specifies the installation angle of 26 degrees of the reception module 2C as the maximum leak angle. When the maximum leak angle does not coincide with the reference angle, the control module 9 determines that the paper sheet 7 is fatigued.

Furthermore, the control module 9 compares the maximum crest value having the largest value with a reference crest value stored in the reference crest value storage module 9*a*. That is, the control module 9 functions as a crest value comparison module.

When the maximum crest value having the largest value is equal to or above the reference crest value stored in the reference crest value storage module 9*a*, the control module 9 determines that the paper sheet 7 is an unimpaired sheet. That is, when the paper sheet 7 is a bank note, the control module 9 judges whether the paper sheet 7 is an unimpaired bank note that can be recirculated or an impaired bank note that is fatigued and cannot be circulated.

Moreover, the when the maximum crest value having the largest value is less than the reference crest value stored in the reference crest value storage module 9*a*, the control module 9 determines that the paper sheet 7 is an impaired sheet.

FIG. 14 is a flowchart for explaining an operation of the stiffness detector 10. It is to be noted that the installation angle of the reception module 2 is preset in accordance with a medium to be examined. As a result, the reference angle is determined.

When the control module 9 in the stiffness detector 10 has detected the paper sheet 7, it applies a pulse signal to the transmission module 1 (a step S11). As a result, the transmission module 1 emits acoustic waves toward the paper sheet 7 from the respective transmission modules 1A, 1B and 10 at the same time. The acoustic waves that have applied to the paper sheet 7 excite Lamb waves in a medium of the paper sheet 7. The excited Lamb waves are propagated through the paper sheet 7 and leak from the paper sheet 7 during propagation, thereby emitting leaky waves.

The reception module 2 in the stiffness detector 10 receives the leaky waves of the Lamb waves exiting from the paper sheet 7 (a step S12).

The control module 9 determines respective maximum crest values in waveforms received by the reception modules 2A, 2B and 2C (a step S13).

The control module 9 specifies a maximum leak angle based on relationships between installation angles of the respective reception modules 2A, 2B and 2C and the maximum crest values (a step S14). That is, the control module 9 specifies the reception module 2 that has measured the maximum crest value having the largest value and determines that the installation angle of the specified reception module 2 as the maximum leak angle.

Here, the control module 9 compares the maximum leak angle specified at the step S14 with a previously determined reference angle (a step S15). Here, when the specified maximum leak angle does not coincide with the reference angle (the step S15, NO), the control module 9 determines that the paper sheet 7 is a fatigued sheet (a step S16). Furthermore, when the specified maximum leak angle coincides with the reference angle (the step S15, YES), the control module 9 determines that the paper sheet 7 is not a fatigued sheet (a step S17).

The control module 9 judges whether the maximum crest value is less than the reference value based on the waveform detected from the paper sheet 7 determined as the fatigued sheet (a step S18). That is, the control module 9 compares the maximum crest value in the waveform received by the reception module 2 installed at the maximum leak angle with the reference crest value stored in the reference crest value storage module 9*a* to judge whether the maximum crest value is less than the reference crest value.

Moreover, the control module 9 judges whether the maximum crest value is less than the reference value based on the waveform detected from the paper sheet 7 determined as a non-fatigued sheet (a step S19). That is, the control module 9 compares the maximum crest value in the waveform received by the reception module 2 installed at the maximum leak value with the reference crest value stored in the reference crest value storage module 9*a* to judge whether the maximum crest value is less than the reference crest value.

When the maximum crest value is determined to be less than the reference value at the step S18 (the step S18, YES), the control module 9 determines that the paper sheet 7 is an impaired sheet (a step S20). That is, the control module 9 determines that the paper sheet 7 is fatigued and not appropriate for recirculation.

When the maximum crest value is determined to be equal to or above the reference value at the step S18 (the step S18, NO), or when the maximum crest value is determined to be equal to or above the reference value at the step S19 (the step S19, NO), the control module 9 determines that the paper sheet 7 is an unimpaired sheet (a step S21). That is, the control module 9 determines that the paper sheet 7 is not fatigued and hence can be recirculated or that the paper sheet 7 is fatigued but can be recirculated.

Additionally, when the maximum crest value is determined to be less than the reference value at the step S19 (the step S19, YES), the control module 9 determines that the paper sheet 7 is an impaired sheet (a step S22). That is, the control module 9 determines that the paper sheet 7 is fatigued and not appropriate for recirculation.

As described above, the stiffness detector according to this embodiment applies acoustic waves to the paper sheet 7. The stiffness detector 10 uses the reception modules 2 arranged at a plurality of different angles to receive the leaky waves of the Lamb waves supplied from the paper sheet 7. The control module 9 in the stiffness detector 10 specifies the maximum crest value and the maximum leak angle based on the received waveform.

The control module 9 compares the previously determined reference angle with the specified maximum leak angle to judge whether the paper sheet 7 is an impaired sheet. Further, the control module 9 compares the previously stored reference crest value with the specified maximum crest value to judge whether the paper sheet 7 is an unimpaired sheet. As a result, a degree of fatigue of the paper sheet 7 can be specified. Furthermore, it is possible to judge whether the paper sheet 7 can be recirculated as an unimpaired sheet in accordance with the degree of fatigue of the paper sheet 7.

As a result, it is possible to provide the stiffness detector and the stiffness detection method that can accurately detect stiffness of the paper sheet and the paper sheet processor including the stiffness detector.

It is to be noted that the three transmission modules 3 are provided in association with the three reception modules in the foregoing embodiment, but one transmission module can suffice. Moreover, although the transmission module 1 is installed at the optimum incidence angle with respect to the paper sheet 7 in the above description, the present invention is not restricted thereto. The transmission module 1 can be installed at any angle as long as the installation angle of the transmission module 1 is an angle at which the Lamb waves can be excited in the paper sheet 7.

Each of FIGS. 15 and 16 is an explanatory view for explaining an example of an arrangement position of the stiffness detector 10.

In an example depicted in FIG. 15, the single stiffness detector 10 is provided at the center of a range where the paper sheet 7 is carried. The stiffness detector 10 examines the range between the transmission module 1 and the reception module 2. Therefore, when the carried paper sheet 7 protrudes from the range between the transmission module 1 and the reception module 2, the plurality of stiffness detectors 10 must be installed in a direction perpendicular to the carrying direction of the paper sheet 7.

In an example shown in FIG. 16, the plurality of stiffness detectors 10 are installed in the direction perpendicular to the carrying direction of the paper sheet 7. In this case, a degree of fatigue of the entire paper sheet 7 can be examined.

FIG. 17 is an explanatory view for explaining another example of arrangement of the transmission module 1 and the reception module 2 in the stiffness detector 10.

As shown in FIG. 17, the stiffness detector 10 includes the transmission module 1 installed on one side and the reception module 2 installed on the other side to sandwich the paper sheet 7 to be carried. Arranging the respective modules in this manner enables preventing acoustic waves emitted from the transmission module 1 from entering the reception module 2 without passing through the paper sheet 7 (crosstalk).

It is to be noted that, when the paper sheet 7 to be carried is slack, relative positions and angles of the paper sheet 7, the transmission module 1 and the reception module 2 vary. Therefore, characteristics of the waveform detected by the stiffness detector 10 change. As a result, the stiffness detector 10 cannot accurately examine the paper sheet 7 in some cases.

Figure 18:
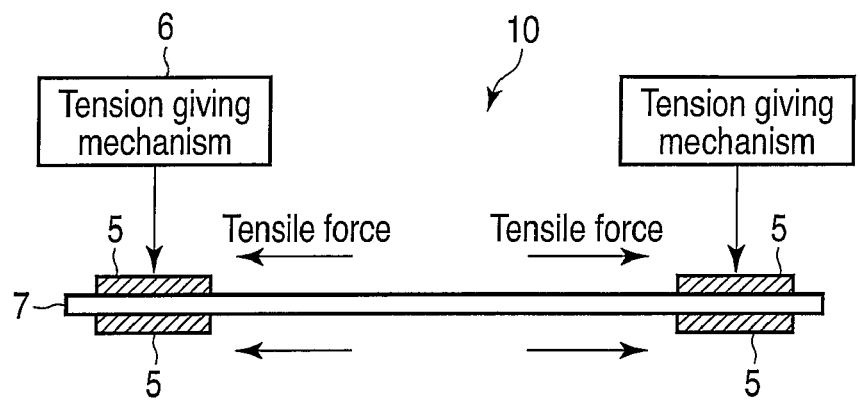
FIG. 18 is an explanatory view for explaining another structural example of a carriage module in the stiffness detector.

FIG. 18 is an explanatory view for explaining an example of another configuration of the carriage module in the stiffness detector 10.

As shown in FIG. 18, the stiffness detector 10 further includes a tension giving mechanism 6. The tension giving mechanism 6 is assembled in the conveying belts 5. The tension giving mechanism 6 applies a force outwards with respect to the conveying belts 5. As a result, the tension giving mechanism 6 generates a tensile force in a direction perpendicular to the carrying direction of the paper sheet 7.

According to this configuration, the paper sheet 7 can be prevented from slacking. As a result, the stiffness detector 10 can accurately examine the paper sheet 7.

Figure 19:
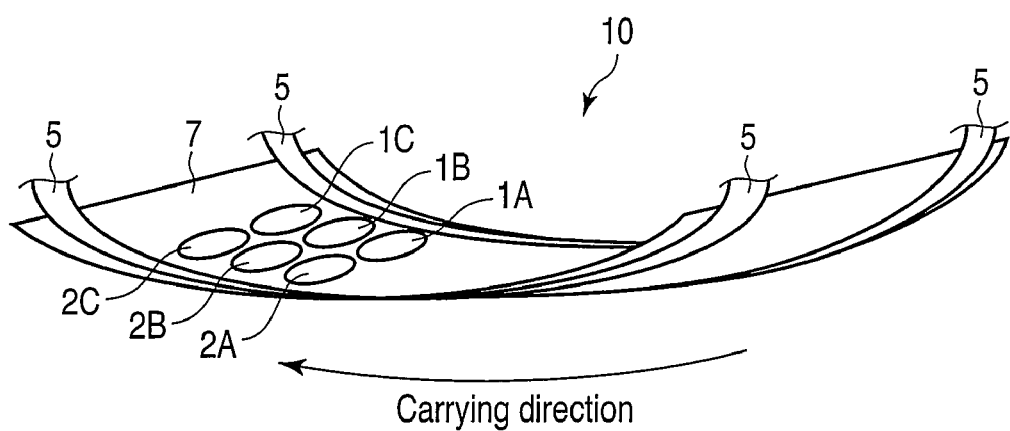
FIG. 19 is an explanatory view for explaining still another example of the carriage module in the stiffness detector.

FIG. 19 is an explanatory view for explaining an example of still another configuration of the carriage module of the stiffness detector 10.

As shown in FIG. 19, the conveying belts 5 of the stiffness detector 10 are installed in a bent state. The conveying belts 5 are installed in contact with, e.g., a non-illustrated driving pulley. As a result, the conveying belts 5 can convey the paper sheet 7 in a bent state.

The conveying belts 5 convey the paper sheet 7 in a bent state to generate a tensile force in a direction perpendicular to the carrying direction of the paper sheet 7. This configuration can prevent the paper sheet 7 from slacking. Consequently, the stiffness detector 10 can accurately examine the paper sheet 7.

A paper sheet processor including the stiffness detector 10 will now be described.

Figure 20:
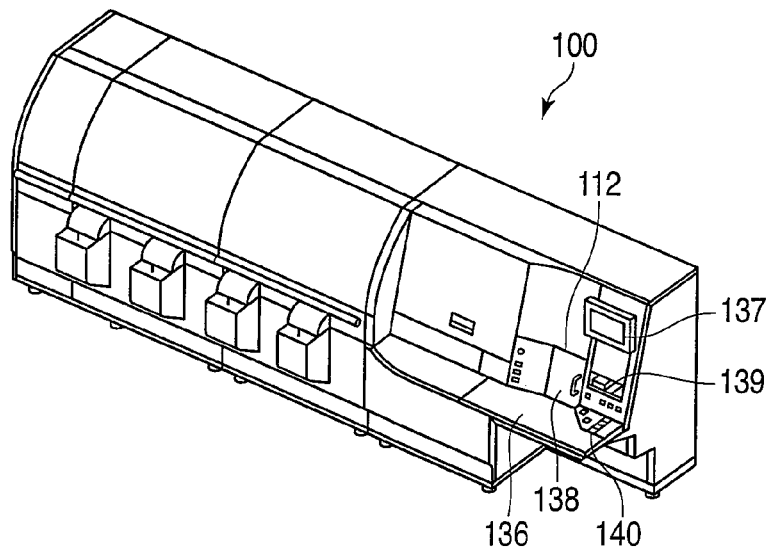
FIG. 20 is an explanatory view for explaining an appearance of a paper sheet processor according to an embodiment.

FIG. 20 is an explanatory view for explaining an appearance of the paper sheet processor according to an embodiment.

As shown in FIG. 20, the paper sheet processor 100 exteriorly includes an injection module 112, an operation module 136, an operation display module 137, a door 138, an ejection opening 139 and a keyboard 140.

The injection module 112 is configured to put in the paper sheet 7. The injection module 112 receives the stacked paper sheets 7 in bulk. The operation module 36 accepts input of various operations performed by an operator. The operation display module 137 displays various kinds of operation guides, processing results and others for the operator. It is to be noted that the operation display module 137 may be configured as a touch panel. In this case, the paper sheet processor 100 detects input of various operations based on buttons displayed in the operation display module 137 and an operation performed by the operator with respect to the operation display module 137.

The door 138 is a door which is utilized to open/close an injection opening of the injection module 112. The ejection opening 139 is configured to take out the paper sheets 7 from an accumulation module where the paper sheets 7 determined to be inappropriate for recirculation by the paper sheet processor 100 are stacked. The keyboard 140 functions as an input module that accepts input of various operations performed by the operator.

Figure 21:
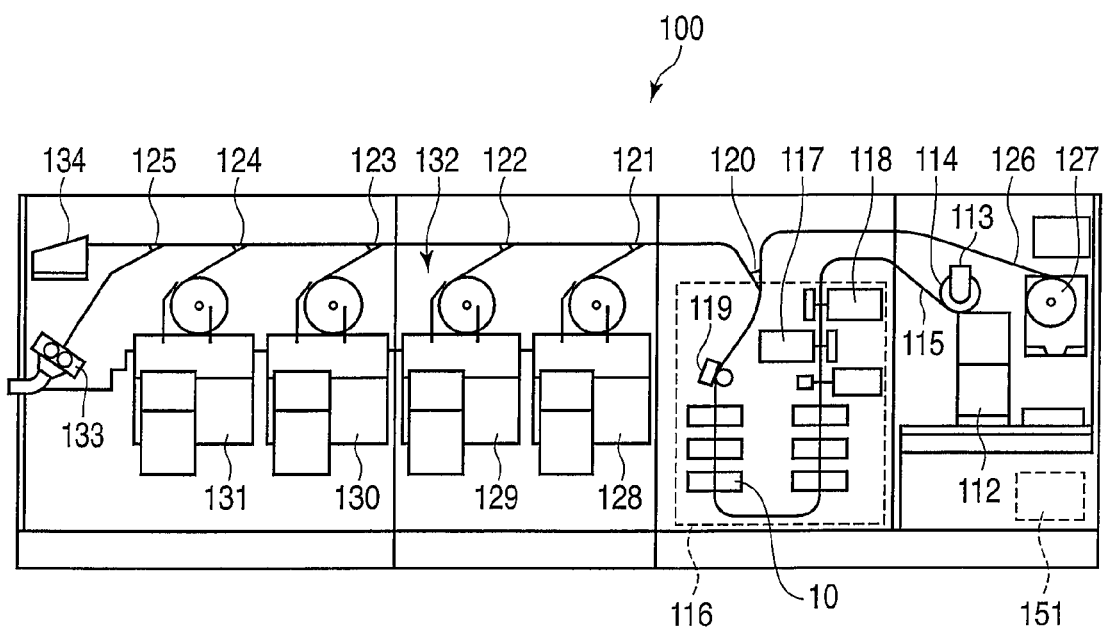
FIG. 21 is an explanatory view for explaining a structural example of the paper sheet processor depicted in FIG. 20.

FIG. 21 is an explanatory view for explaining a structural example of the paper sheet processor 100 depicted in FIG. 20.

The paper sheet processor 100 includes the injection module 112, an ejection module 113, an adsorption roller 114, a carrier path 115, an examination module 116, gates 120 to 125, a rejection carrier path 126, a rejection accumulation module 127, accumulation/bundling modules 128 to 131, a cutting module 133 and a stacker 134. Further, the paper sheet processor 100 includes a main control module 151. The main control module 151 integrally controls operations of the respective modules in the paper sheet processor 100.

The ejection module 113 is provided above the injection module. The ejection module 113 includes the adsorption roller 114. The adsorption roller 114 is provided to be in contact with an upper end of the paper sheet 7 set in the injection module 112 in an accumulating direction. That is, when the adsorption roller 114 rotates, it takes in the papers sheets 7 set in the injection module 112 one by one from the upper end in the accumulating direction into the processor. For example, when the adsorption roller 114 functions to take out one paper sheet 7 every time it makes one revolution. As a result, the adsorption roller 114 takes out the paper sheets 7 at a fixed pitch. The paper sheets 7 taken in by the adsorption roller 114 are introduced into the carrier path 115.

The carrier path 115 is carrying means for carrying the paper sheets 7 to the respective modules in the paper sheet processor 100. The carrier path 115 includes the conveying belts 5, a non-illustrated driving pulley and others. The carrier path 115 uses non-illustrated driving motor and driving pulley to operate the carrying belts 5. The carrier path 115 carries the paper sheets 7 taken in by the adsorption roller 114 at a fixed speed by using the conveying belts 5. It is to be noted that a side of the carrier path 115 close to the ejection module 113 is an upstream side and a side of the same close to the stacker 134 is a downstream side in the following description.

The examination module 116 is provided on the carrier path 115 extending from the ejection module 113. The examination module 116 includes an image reader 117, an image reader 118, a stiffness detector 10 and a thickness examiner 119. The examination module 116 detects optical characteristic information, mechanical characteristics and magnetic feature information of the paper sheet 7. As a result, the paper sheet processor 100 examines a type, fouling damages, front and back sides, authenticity and others of the paper sheet 7.

The image readers 117 and 118 are provided to face each other with the carrier path 115 interposed therebetween. The image readers 117 and 118 read images on both surfaces of the paper sheet 7 carried through the carrier path 115. Each of the image readers 117 and 118 includes a charge coupled device (CCD) camera. The paper sheet processor 100 acquires pattern images on the front surface and the back surface of the paper sheet 7 based on images acquired by the image readers 117 and 118.

The image readers 117 and 118 temporarily stores the read images in a non-illustrated memory in the examination module 116. The paper sheet processor 100 displays the images stored in this memory in the operation display module 137 in accordance with operation inputs.

The stiffness detector 10 detects mechanical characteristics of the paper sheet 7 as described above. As a result, the stiffness detector 10 judges whether the paper sheet 7 is an impaired sheet that is fatigued and cannot be recirculated or whether it is an unimpaired sheet that can be recirculated.

The thickness examination module 119 examines a thickness of the paper sheet 7 carried through the carrier path 115. For example, when the detected thickness is equal to or above a specified value, the paper sheet processor 100 detects a state that the two paper sheets 7 have been taken at the same time.

Furthermore, the examination module 116 includes a non-illustrated magnetic sensor and others. The magnetic sensor detects magnetic characteristic information of the paper sheet 7.

The main control module 151 judges whether the paper sheet 7 is an unimpaired sheet, an impaired sheet or a rejected sheet based on detection results obtained from the image readers 117 and 118, the stiffness detector 10, the thickness examination module 119, the magnetic sensor and others.

The paper sheet processor 100 carries the paper sheet 7 determined as an unimpaired sheet to the accumulation/bundling modules 128 to 131. Furthermore, the paper sheet processor 100 carries the paper sheet 7 determined as an impaired sheet to the cutting module 133. The cutting module 133 cuts the carried impaired sheet. It is to be noted that the paper sheet processor 100 may carry the impaired sheet to the stacker 134 to be stacked. The stacker 134 performs sealing every time the number of the stacked impaired sheet reaches, e.g., 100.

The rejected sheet is the paper sheet 7 which does not correspond to the unimpaired sheet and the impaired sheet. The paper sheet processor 100 carries the paper sheet 7 determined as the rejected sheet to the rejection accumulation module 127. The rejected sheet includes, e.g., an abnormally carried sheet such as a sheet taken with the other note at the same time, a defective sheet such as a folded or worn sheet, and an unrecognizable sheet such as an unapplied note type or a false sheet.

The gates 120 to 125 are sequentially arranged on the carrier path 115 on the downstream side of the examination module 116. Each of the gates 120 to 125 is controlled by the main control module 151. The main control module 151 controls operations of the respective gates 120 to 125 based on a result of examination executed by the examination module 116. As a result, the main control module 151 controls to carry the paper sheet 7 that is being carried through the carrier path 115 to a predetermined processing module.

The gate 120 arranged right behind the examination module 116 branches the carrier path 115 to the rejection carrier path 126. That is, the gate 120 is switched in such a manner that a rejected sheet determined as a non-genuine sheet as a result of examination executed by the examination module 116 or a non-testable sheet that cannot be subjected to examination by the examination module 116 is carried to the rejection carrier path 126.

The rejection accumulation module (a rejection module) 127 is provided at a trailing end of the rejection carrier path 126. The rejection accumulation module 127 accumulates the above-described rejected sheet or non-testable sheet while keeping a posture when taken out from the rejection module 113. The paper sheet 7 accumulated in the rejection accumulation module 127 can be taken out from the ejection opening 139.

Further, the accumulation/bundling modules 128 to 131 (which are generically called an accumulation/bundling module 132) are provided at branch destinations from the gates 121 to 124, respectively. The paper sheets 7 which can be recirculated are classified in accordance with a type and a front or back surface and then accumulated. The accumulation/bundling module 132 bundles a predetermined number of the accumulated paper sheets 7 at a time to be stored. Furthermore, the paper sheet processor 100 uses a non-illustrated high-bulk bundling module to accumulate and bundle a plurality of bundles each including the predetermined number of paper sheets 7.

The cutting module 133 is arranged at a branch destination from the gate 125. The cutting module 133 cuts and accommodates the paper sheets 7. The paper sheets 7 carried to the gate 125 are the proper paper sheet 7 and the paper sheet 7 (an impaired sheet) determined as being unable to be recirculated.

Moreover, the stacker 134 is arranged at a destination of the other carrier path branching from the gate 125. The main control module 151 controls the gate 125 to carry the paper sheet 7 to the cutting module 133 when an impaired sheet cutting mode is selected. Additionally, the main control module 151 controls the gate 125 to carry the paper sheet 7 to the stacker 134 when the impaired sheet cutting mode is not selected.

It is to be noted that the main control module 151 sequentially stores the number of the paper sheets 7 accumulated in the accumulation/bundling module 132, the number of the paper sheets 7 cut by the cutting module 133 and identifying information.

Figure 22:
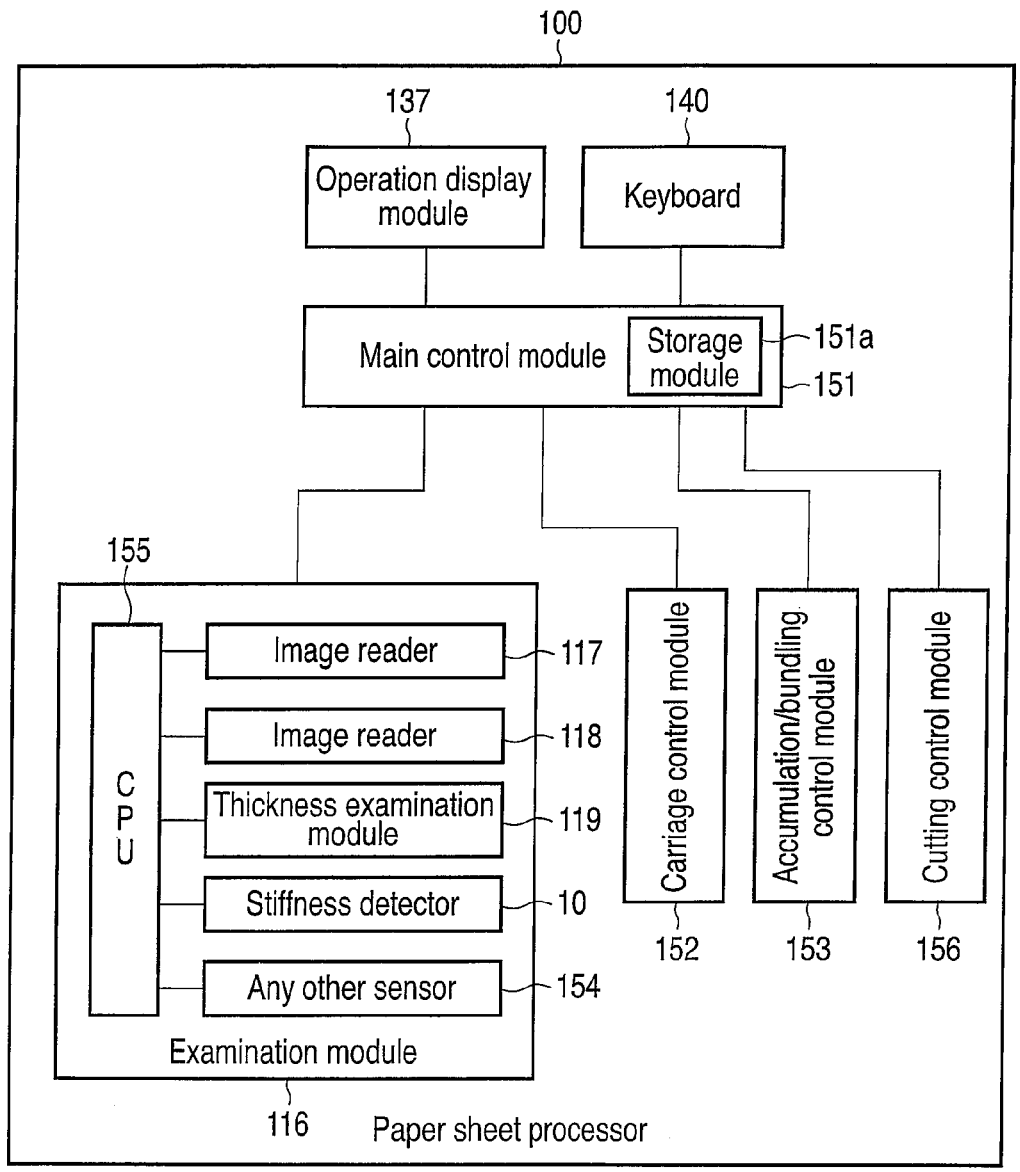
FIG. 22 is a block diagram for explaining a structural example of a control system in the paper sheet processor depicted in FIGS. 20 and 21.

FIG. 22 is a block diagram for explaining a structural example of a control system in the paper sheet processor 100 depicted in FIGS. 20 and 21.

The paper sheet processor 100 includes the main control module 151, the examination module 116, the carriage control module 152, an accumulation/bundling control module 153, a cutting control module 156, the operation display module 137, the keyboard 140 and others.

The main control module 151 controls the entire paper sheet processor 100. The main control module 151 controls the carriage control module 152 and the accumulation/bundling control modules 153 based on an operation input through the operation display module 137 and a result of examination executed by the examination module 116.

For example, an operator uses the operation display module 137 or the keyboard 140 to input a sheet type, the number, a wear judgment level, a name of a supply source, a processing method and others of the paper sheet 7 to be processed.

The examination module 116 includes the image readers 117 and 118, the thickness examination module 119, the stiffness detector 10, any other sensor 154 and a CPU 155.

The image readers 117 and 118 read images on both surfaces of the paper sheet 7 carried through the carrier path 115. Each of the image readers 117 and 118 includes a light receiving element such as a CCD and an optical system. Each of the image readers 117 and 118 projects light onto the carried paper sheet 7 and receives reflected light or transmitted light by using the optical system. Each of the imager readers 117 and 118 forms an image of the light received through the optical system onto the CCD to acquire an electric signal (an image).

The main control module 151 stores an image that serves as a reference for the paper sheet 7 (a reference image) in a storage module 151a in advance. The main control module 151 compares an image acquired from the paper sheet 7 with the reference image stored in the storage module 151a to make a wear judgment and a false note judgment.

As described above, the stiffness detector 10 uses the transmission module 1 to apply acoustic waves to the carried paper sheet 7. The stiffness detector 10 uses the plurality of reception modules 2A, 2B and 2C arranged at a plurality of different angles with respect to the paper sheet 7 to receive leaky waves of Lamb waves emitted from the paper sheet 7. The control module 9 of the stiffness detector 10 specifies a maximum crest value and a maximum leak angle based on waveforms received by the respective reception modules 2.

The control module 9 compares a reference angle previously determined based on characteristics of the paper sheet 7 with the specified maximum leak angle to judge whether the paper sheet 7 is a fatigued sheet. Further, the control module 9 compares a reference crest value stored in the reference crest value storage module 9a with the specified maximum crest value to judge whether the paper sheet 7 is an unimpaired sheet. As a result, the stiffness detector 10 can judge whether the paper sheet 7 can be recirculated as the unimpaired sheet.

The thickness examination module 119 examines a thickness of the paper sheet 7 carried through the carrier path 115.

Any other sensor 154 is, e.g., a magnetic sensor. The magnetic sensor detects magnetic characteristic information from the paper sheet 7 carried through the carrier path 115.

The CPU 155 judges a type, wear, front and back surfaces, authenticity and others of the paper sheet 7 carried through the carrier path 115 based on results of examination executed by the image readers 117 and 118, the thickness examination module 119, the stiffness detector 10, any other sensor 154 and others.

The carriage control module 152 controls the ejection module 113, the carrier path 115, rejection carrier path 126 and the gates 120 to 125 under control of the main control module 151. As a result, the carriage control module 152 controls fetch and carriage of the paper sheet 7. Furthermore, the carriage control module 152 executes classification processing for classifying the determined paper sheets 7 in accordance with each type. That is, the carriage control module 152 functions as a classification processing module. It is to be noted that the carriage control module 152 performs classification in accordance with each type of the paper sheet 7, but it is not restricted thereto. For example, the paper sheet 7 may be classified and processed in accordance with a degree of fatigue based on an examination result obtained by the stiffness detector 10.

The accumulation/bundling control module 153 controls the rejection accumulation module 127 and the accumulation/bundling modules 128 to 131 under control of the main control module 151. As a result, the accumulation/bundling control module 153 controls accumulation and bundling of the paper sheet 7.

The cutting control module 156 controls operations of the cutting module 133 under control of the main control module 151. As a result, the cutting module 133 cuts the carried paper sheet 7.

As described above, the paper sheet processor 100 including the stiffness detector 10 according to an embodiment of the present invention examines the paper sheet 7 by using the stiffness detector 10. The stiffness detector 10 examines mechanical characteristics of the paper sheet 7 and judges whether the paper sheet 7 can be recirculated. The paper sheet processor 100 can appropriately process the paper sheet 7 based on a judgment result.

It is to be noted that the description has been given on the assumption that the carried paper sheet 7 is examined in the foregoing embodiment, but the present invention is not restricted to this configuration. The paper sheet 7 which remains stationary can be likewise examined.

Figure 23:
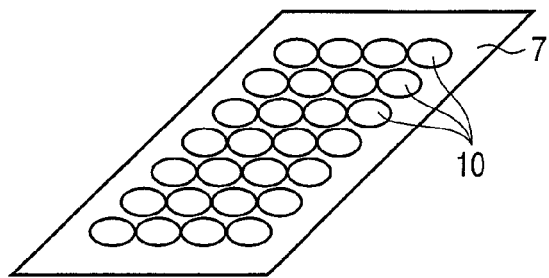
FIG. 23 is an explanatory view for explaining another example of the arrangement position of the stiffness detector.

FIG. 23 is an explanatory view for explaining another arrangement example of the stiffness detector 10. In the example shown in FIG. 23, a description will be given on the assumption that the paper sheet 7 is not carried.

When examining the entire paper sheet 7 in a state that the paper sheet 7 is not carried, the plurality of stiffness detectors 10 are installed in a matrix pattern as shown in FIG. 23. Adopting such arrangement enables detecting stiffness of the entire paper sheet 7.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stiffness detector comprising:
    a transmission module configured to transmit acoustic waves to a paper sheet at a predetermined angle and thereby excite Lamb waves;
    a reception module including a plurality of reception sensors which receive leaky waves of the Lamb waves propagated through the paper sheet at different angles with respect to the paper sheet; and
    a first judgment module configured to specify a maximum leak angle at which a leak amount of the acoustic waves from the paper sheet becomes maximum based on outputs from the plurality of reception sensors in the reception module and to judge a degree of fatigue of the paper sheet based on the specified maximum leak angle.

2. The stiffness detector according to claim 1, wherein the first judgment module determines that the paper sheet is fatigued when the specified maximum leak angle does not coincide with a previously determined reference angle.

3. The stiffness detector according to claim 1, further comprising:
    a reference crest value storage module configured to store a reference crest value in advance;
    a crest value comparison module configured to specify a maximum crest value based on outputs from the plurality of reception sensors in the reception module and to compare the specified maximum crest value with a reference crest value stored in the reference crest value storage module; and
    a second judgment module configured to judge whether the paper sheet is an unimpaired sheet based on a comparison result obtained by the crest value comparison module.

4. The stiffness detector according to claim 3, wherein the second judgment module determines the paper sheet as an impaired sheet when the specified maximum crest value is less than the reference crest value stored in the reference crest value storage module.

5. The stiffness detector according to claim 2, wherein the transmission module is disposed on one surface of the paper sheet at the reference angle.

6. The stiffness detector according to claim 5, wherein the reception module comprises: a first reception sensor disposed on one surface of the paper sheet at the reference angle; a second reception sensor disposed at an angle of the reference angle+N degrees; and a third reception sensor disposed at an angle of the reference angle−M degrees.

7. The stiffness detector according to claim 6, further comprising a shielding plate configured to shield against the acoustic waves on one surface of the paper sheet between the transmission module and the reception module.

* * * * *